United States Patent [19]

Chan

[11] 4,391,759

[45] Jul. 5, 1983

[54] PROCESS FOR THE PREPARATION OF ORGANOTHIOALDOXIME COMPOUNDS

[75] Inventor: John K. Chan, Charleston, W. Va.

[73] Assignee: Union Carbide Corporation, Danbury, Conn.

[21] Appl. No.: 247,368

[22] Filed: Mar. 25, 1981

[51] Int. Cl.³ .............................................. C07C 119/18
[52] U.S. Cl. .................................................. 260/453.3
[58] Field of Search ...................................... 260/453.3

[56] References Cited

U.S. PATENT DOCUMENTS

| 3,535,361 | 10/1970 | Anders et al. | 260/453.3 |
| 3,574,736 | 4/1971 | Fuchs | 260/453.3 |
| 3,658,869 | 4/1972 | Soloway et al. | 260/453.3 |
| 3,752,841 | 8/1973 | Fuchs | 260/453.3 |
| 3,778,475 | 12/1973 | Fuchs | 260/453.3 |
| 3,987,096 | 10/1976 | Fuchs | 260/453.3 |
| 4,144,261 | 3/1979 | Chan | 260/453.3 |

Primary Examiner—Henry R. Jiles
Assistant Examiner—Robert C. Whittenbaugh
Attorney, Agent, or Firm—G. L. Coon; W. R. Moran; J. A. Shedden

[57] ABSTRACT

An improved process for preparing 1-organothioaldoxime compounds by reacting an aldoxime or α-hydroxyiminoketone with an alkaline hypohalite in an acidic medium and reacting the resulting 1-haloaldoxime with the alkali metal salt of a mercaptan, said acidic medium comprising an acid added in an amount of from about 0.5 to about 4.0 equivalents for each mole of alkaline hypohalite used.

22 Claims, No Drawings

PROCESS FOR THE PREPARATION OF ORGANOTHIOALDOXIME COMPOUNDS

FIELD OF THE INVENTION

This invention relates generally to a process for preparing oxime compounds and, more particularly, to a process for preparing 1-organothioaldoxime compounds.

BACKGROUND OF THE INVENTION

This invention relates to an improved process for preparing 1-organothioaldoxime compounds. More particularly, this invention is directed to a method of preparing 1-organothioaldoxime compounds by reacting an aldoxime or α-hydroxyiminoketone with an alkaline hypohalite in an acidic medium and reacting the resulting 1-haloaldoxime with the alkali metal salt of a mercaptan, said acidic medium comprising an acid added in an amount of from about 0.5 to about 4.0 equivalents for each mole of alkaline hypohalite used.

1-Organothioaldoxime compounds and their preparation by the chlorination of an aldoxime or α-hydroxyiminoketone followed by reaction with a sodium mercaptide are well known. U.S. Pat. No. 3,658,869 discloses a two-step process for preparing 1-hydrocarbylthioaldoximes in an aqueous reaction medium (essentially only water) by the halogenation of an aldoxime followed by reaction with a mercaptan in the presence of a base. The 1-hydrocarbylthioaldoximes are useful as oil additives, antioxidants, accelerators for curing rubber and as chemical intermediates. U.S. Pat. No. 3,535,361 describes a three-step process for the preparation of N-hydroxyimidothiocarboxylic acid esters which includes (1) reacting an aldehyde with a hydroxylamine in an aqueous medium to form the corresponding aldehydoxime, (2) acidifying the resulting reaction medium to a pH of at most 1 and reacting aldehydoxime with chlorine to form the corresponding chlorinated aldehydoxime and (3) reacting the chlorinated aldehydoxime with a mercapto compound to a pH of at most 1 to form the corresponding N-hydroxyimidothiocarboxylic acid ester. The N-hydroxyimidothiocarboxylic acid esters are useful as intermediates in the preparation of auxiliaries for plastics and pesticides. U.S. Pat. No. 3,778,475 relates to a process for the preparation of hydroxamoyl chlorides which includes reacting certain α-hydroxyiminoketones with elemental chlorine in an aqueous medium and under acidic conditions at a temperature of about −15° to 30° C. The hydroxamoyl chlorides obtained in this process are useful intermediates to thiolhydroxamate esters and carbamates having insecticidal properties. However, the main drawback of the above-mentioned prior art processes is low yield of the desired product.

U.S. Pat. No. 3,752,841 relates to the chlorination of aldoximes in a solvent containing at least 10% by weight of dimethylformamide (DMF) to form alkylhydroxamic acid chlorides which can then be converted to alkylthiohydroxamates by reaction with a mercaptan and base in the presence of the same solvent containing at least 10% by weight of dimethylformamide. The alkylthiohydroxamates can then be converted in the same solvent to alkylthiohydroxamate carbamates which are useful as insecticides. This process also suffers from a number of inherent disadvantages. The separation problems of the alkylthiohydroxamate compounds disclosed in this patent are complicated by the use of dimethylformamide since these compounds are very soluble in dimethylformamide. This makes it necessary to use costly, elaborate and cumbersome purification procedures, such as distillation, solvent extraction and the like, to isolate the final product.

U.S. Pat. No. 4,144,261 describes an improved process for preparing 1-organothioaldoxime compounds by chlorinating the corresponding aldoxime and reacting the resulting 1-haloaldoxime with the sodium salt of a mercaptan, the improvement which comprises conducting the process in an aqueous solvent containing from 5 to 75 percent by weight of a linear or cyclic polyhydric alcohol having from 2 to 20 carbon atoms. U.S. patent application Ser. No. 188,669, filed Sept. 19, 1980, discloses an improved method for preparing 1-organothioaldoxime compounds by chlorinating an α-hydroxyiminoketone and reacting the resulting 1-haloalkoxime with an alkali metal salt of a mercaptan, the improvement which comprises conducting the process in an aqueous solvent containing from about 5 to 75 percent by weight of a simple alcohol having from 1 to 4 carbon atoms or a linear or cyclic polyhydric alcohol having from 2 to 20 carbon atoms. However, neither of these two prior art references and no prior art is currently known to us which discloses, teaches or suggests the advantageous properties, i.e., enhanced yields, obtained by utilizing the claimed process of this invention.

It is desirable, therefore, and is a primary object of this invention, to provide an improved process for obtaining enhanced yields of 1-organothioaldoxime compounds by reacting an aldoxime or α-hydroxyiminoketone with an alkaline hypohalite in an acidic medium and reacting the resulting 1-haloaldoxime with the alkali metal salt of a mercaptan, said acidic medium comprising an acid added in an amount of from about 0.5 to about 4.0 equivalents for each mole of alkaline hypohalite used.

A further object of this invention is to provide additional flexibility in the choice of alternative reactants and processing conditions for the production of 1-organothioaldoxime compounds.

Various other objects and advantages of this invention will become apparent to those skilled in the art from the accompanying description and disclosure.

SUMMARY OF THE INVENTION

According to the present invention there is provided an improved process for preparing organothioaldoxime compounds of the formula:

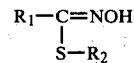

by the steps of:
(a) reacting an aldoxime of the formula:
$R_1CH=NOH$

or an α-hydroxyiminoketone of the formula:

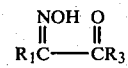

with an alkaline hypohalite in an acidic medium to form the corresponding 1-haloaldoxime, said acidic medium comprising an acid added in an amount of from about 0.5 to about 4.0 equivalents for each mole of alkaline hypohalite used; and (b) reacting said 1-haloaldoxime with an alkali metal mercaptide salt of the formula:

R₂SM to form said organothioaldoxime compound, wherein the reactions of said steps (a) and (b) are conducted in an aqueous medium and wherein M denotes an alkali metal cation and $R_1$, $R_2$ and $R_3$ are individually alkyl, alkoxyalkyl, cycloalkyl, phenyl or phenylalkyl, all of which may be either unsubstituted or substituted with one or more alkyl, halo, alkoxy, cyano, nitro or dialkylamino substituents.

DESCRIPTION OF THE PREFERRED EMBODIMENTS

The halogenation reaction of step (a) to form the 1-haloaldoxime reactant is conveniently performed by reacting the alkaline hypohalite and the aldoxime or α-hydroxyiminoketone in an aqueous acidic medium. Ideally, the aqueous acidic medium and the alkaline hypohalite reactant are simultaneously introduced into the reaction mixture. Illustrative of preferred acids that are useful as an acidic medium for this reaction are mineral acids such as hydrochloric acid, sulfuric acid, phosphoric acid and the like. The most preferred acid is hydrochloric acid. Organic acids are also useful as an acidic medium for this reaction. Suitable organic acids include benzenesulfonic acid, toluenesulfonic acid, acetic acid, propionic acid and the like. The aqueous acidic medium preferably contains from about 0.5 to about 4.0 equivalents of acid for each mole of alkaline hypohalite reactant. Most preferably, the aqueous acidic medium contains from about 1 to about 2 equivalents of acid for each mole of alkaline hypohalite reactant. The use of an excess of acid does not affect the reaction efficiency.

The alkaline hypohalite used as the halogenating agent can be prepared easily by the well known reaction of a halogen with aqueous caustic solution, as described in *Organic Synthesis*, Coll. Vol. IV, p. 74 for the preparation of sodium hypochlorite, incorporated herein by reference. The preferred concentration of alkaline hypohalite contained in water is from about 1 to about 40 percent by weight. The most preferred concentration of alkaline hypohalite contained in water is from about 5 to about 30 percent by weight. Illustrative of preferred alkaline hypohalites useful in the process of this invention includes sodium hypochlorite, calcium hypochlorite, potassium hypochlorite and the like. The most preferred alkaline hypohalite useful in the process of this invention is sodium hypochlorite. Generally, a stoichiometric amount of the alkaline hypohalite is required to react with the aldoxime or α-hydroxyiminoketone reactant to form the 1-haloaldoxime intermediate. However, it is preferred to employ the alkaline hypohalite in an amount of from about 10 to about 25 percent molar excess based on the total weight of aldoxime or α-hydroxyiminoketone reactant. Most preferably, the alkaline hypohalite is employed in an amount of from about 15 to about 20 percent molar excess based on the total weight of aldoxime or α-hydroxyiminoketone reactant.

In general the aldoxime reactants that are useful in the conduct of the process of this invention are well known to those skilled in the art. The aldoxime may be either an unsubstituted or substituted alkyl, cycloalkyl, alkoxyalkyl, aryl or aralkyl compound. Illustrative of the preferred aldoxime reactants are alkanaldoximes such as acetaldoxime, propionaldoxime, isobutyraldoxime, n-valeraldoxime and the like. The most preferred aldoxime reactant is acetaldoxime. Also useful are the cyclic aldoximes and aromatic aldoximes, i.e. those compounds in which R is cyclic groups such as cyclohexane, cyclopentane, cycloheptane, alkoxyalkyl groups such as methoxymethyl, ethoxymethyl, proproxymethyl or aromatic groups such as benzene, p-methylbenzene, p-ethylbenzene, benzyl, phenethyl and the like. As previously noted these radicals may be suitably substituted with non-reactive functional groups, such as cyano, halo, nitro or alkyl groups.

The aldoxime compounds utilized as a reactant in the process of this invention can be conveniently prepared according to conventional methods. For example, these compounds can be conveniently prepared by reacting an appropriate aldehyde with hydroxylamine salts, optionally in the presence of an alkali metal hydroxide or carbonate. Another method involves reacting the corresponding aldehyde in a water medium with sodium nitrite, sodium bisulfite and sulfur dioxide.

In general the α-hydroxyiminoketone reactants that are useful in the conduct of the process of this invention are well known to those skilled in the art. Illustrative of the preferred α-hydroxyiminoketone reactants include 3-hydroxyimino-2-butanone (biacetyl monoxime), 3-hydroxyimino-1-methoxy-2-butanone, isonitrosopropiophenone, 3-hydroxyimino-2,4-pentanedione, ethyl-2-hydroxyiminoacetoacetate, 2-hydroxyimino-N,N-dimethylacetoacetamide and the like. The most preferred α-hydroxyiminoketone reactant is 3-hydroxyimino-2-butanone (biacetyl monoxime).

The α-hydroxyiminoketone compounds utilized as a reactant in the process of this invention can be readily synthesized from the corresponding ketones by reaction with nitrous acid, as described in *Organic Synthesis*, Coll. Vol. II, pp. 204–208 for the preparation of 3-hydroxyimino-2-butanone (biacetyl monoxime), incorporated herein by reference. Upon halogenation of the 3-hydroxyimino-2-butanone reactant in accordance with the process of the present invention, the molecule cleaves to form the 1-haloaldoxime intermediate of the formula $(R_1)C(X)=NOH$ and a carboxylic acid of the formula $R_3COOH$ wherein X is halogen and $R_1$ and $R_3$ are defined above.

The quantity of the aldoxime or α-hydroxyiminoketone reactant employed in the process of this invention is preferably from about 5 to about 75 percent by weight based on the total weight of the aqueous medium. The most preferred amount is from about 10 to about 25 percent by weight based on the total weight of the aqueous medium. Greater amounts of aqueous medium can of course be used, except such amounts merely dilute the reactants in the reaction mass with no particular advantage being obtained.

The 1-haloaldoxime intermediate of the halogenation step may be isolated and purified for use at some later time or it may be reacted with the mercaptide salt without purification or isolation. The preferred 1-haloaldoxime intermediate of the present invention is acethydroxamoyl chloride.

The mercaptide salts utilized as reactants in the process of this invention as well as their method of preparation are well known to those skilled in the synthetic arts. The mercaptide salt reactant can be conveniently prepared by treating the corresponding mercaptan with a base.

The base employed should be of sufficient basicity and quantity to form a salt of the mercaptan. Also, an additional quantity of base must be added in an amount sufficient to neutralize the carboxylic acid by-product formed when α-hydroxyiminoketone is used as the starting reactant. The additional quantity of base may alternatively be added before or after the addition of mercaptide salt to the reaction mixture to insure complete reaction. The preferred amount of base is from about 50 to about 300 molar percent excess, most preferably 100 to 200 molar percent excess, based on the amount of aldoxime or α-hydroxyiminoketone reactant employed.

Useful mercaptan (thiols) include the alkyl mercaptans such as methyl mercaptan, ethyl mercaptan, propyl mercaptan, isopropyl mercaptan, hexyl mercaptan, isobutyl mercaptan, pentyl mercaptan, decyl mercaptan and the like. Other useful mercaptans are those in which $R_2$ is a cyclic group such as cycloheptane, cyclohexane, cyclopentane, cyclobutane or the like; those in which $R_2$ is an alkoxyalkyl group such as methoxymethyl, propoxymethyl, methoxyethyl or the like; or those in which $R_2$ is an aromatic group such as benzene, 2-methylbenzene, 3-alkoxybenzene, benzyl, phenethyl and the like. As previously noted these radicals may be suitably substituted with non-reactive functional groups such as halogen, cyano (e.g., 2-cyanoethyl mercaptan), alkyl, nitro, etc. Methyl mercaptan is preferred for use in the process of this invention.

Suitable organic bases include the alkali metal alkoxides such as sodium methoxide, sodium ethoxide and the like.

Useful inorganic bases include the alkali metal and the alkaline earth metal carbonates such as lithium, sodium, potassium, calcium and barium carbonate; the alkali metal bicarbonates such as sodium bicarbonate, potassium bicarbonate and the like; the alkali metal hydroxides such as lithium hydroxide, sodium hydroxide, potassium hydroxide and the like. Inorganic bases are preferred for use in the process of this invention. Sodium hydroxide is the most preferred inorganic base for use in the process of this invention.

The mercaptide salt reactant may be generated outside the presence of the 1-haloaldoxime reactant and used at some latter date. Alternatively, the mercaptide salt reactant may be generated in situ, i.e. in presence of the 1-haloaldoxime reactant. The preferred mercaptide salt reactant for use in the process of this invention is sodium methyl mercaptide.

In general, the 1-haloaldoxime reactant is reacted with a stoichiometric quantity of the mercaptide salt, although, it should be understood that the preferred quantity of mercaptide salt employed can vary from about stoichiometric to about 50 percent molar excess based on the total weight of 1-haloaldoxime reactant. In the most preferred embodiment of this reaction, the quantity of mercaptide salt employed will vary from about 5 to about 25 percent molar excess based on the total weight of 1-haloaldoxime reactant.

The halogenation reaction of step (a) above and the mercaptide reaction of step (b) above are preferably conducted in an aqueous medium. The most preferred aqueous medium useful in the process of this invention is water. Additionally, the halogenation reaction of step (a) is conducted in an acidic medium as described above. Water has the advantage that the reactants are soluble and it is also very cheap. Other inert solvents and/or mixed solvents systems may also be useful; for example, methanol, ethanol, isopropanol, ethylene glycol, glycerol and the like including mixtures thereof. Aqueous mixtures of these inert solvents and/or mixed solvents systems may also be useful in the process of this invention.

As described hereinabove in the structural formulas of the organothioaldoxime compound, aldoxime reactant, α-hydroxyiminoketone reactant, 1-haloaldoxime intermediate, carboxylic acid by-product and alkali metal mercaptide salt, $R_1$, $R_2$ and $R_3$ are individually alkyl, alkoxyalkyl, cycloalkyl, phenyl or phenylalkyl, all of which may be either unsubstituted or substituted with one or more alkyl, halo, alkoxy, cyano, nitro or dialkylamino substituents. A preferred embodiment of the process of this invention includes those compounds wherein $R_1$, $R_2$ and $R_3$ are individually cyanoalkyl or nitroalkyl having from 1 to 8 carbon atoms. A further preferred embodiment of the process of this invention includes those compounds wherein $R_1$, $R_2$ and $R_3$ are individually methyl, ethyl or propyl. Yet another preferred embodiment of the process of this invention includes those compounds wherein $R_1$, $R_2$ and $R_3$ are methyl.

The reaction temperature for the halogenation and the mercaptide addition steps is not critical and can be varied over a wide range. The reactions can be conducted at a temperature in the range of from about $-20°$ C. to approximately $40°$ C. Preferred reaction temperatures are from about $-10°$ C. to about $15°$ C. with particularly preferred reaction temperatures being from about $0°$ C. to about $-10°$ C. At temperatures below $-20°$ C. the rate of reaction becomes markedly slower, while at temperatures above $40°$ C. product degradation and side reaction may occur.

Reaction pressures are not critical. The process of this invention can be conducted at either subatmospheric, atmospheric or superatmospheric pressure. For convenience, the reaction is usually conducted at atmospheric or autogenous pressure.

The process of this invention is carried out over a period of time sufficient to produce the desired 1-organothioaldoxime compound in adequate yield. The preferred 1-organothioaldoxime compound prepared by the process of this invention is S-methyl-N-hydroxythioacetimidate. In general, residence times can vary from about a few minutes to 24 hours or longer. When the reaction is conducted at a temperature of from $-10°$ C. to $15°$ C., a time of from 1 to 9 hours is necessary for the halogenation reaction of step (a) and a 1 to 2 hour contact time is necessary for the mercaptide reaction of step (b). The preferred reaction time for the halogenation reaction of step (a) is from 2 to 6 hours. The most preferred reaction time for the halogenation reaction of step (a) is 6 hours. Under the preferred conditions, somewhat longer times do not affect the product yields; shorter times make it difficult to control the reaction temperature and render lower yields of reaction product. Reaction time is influenced to a significant degree by the reactants, the reaction temperature, the concentration and choice of base, the choice and concentration of reaction solvent, and by other factors known to those skilled in the art.

The process described herein for the production of 1-organothioaldoxime compounds, particularly S-methyl-N-hydroxythioacetimidate, is quite simple. An aqueous solution of sodium hypochlorite and a solution of hydrochloric acid are fed simultaneously or incrementally to an aqueous mixture containing acetaldoxime or biacetyl monoxime over a period of 5 to 6 hours at a temperature of from −5° C. to −10° C. Following the chlorination reaction, an aqueous solution of sodium methyl mercaptide is added at the same reaction temperature. It is preferred to add the sodium methyl mercaptide solution to the reaction mixture containing the acethydroxamoyl chloride rather than adding methyl mercaptan first and then adding sodium hydroxide afterwards. After completion of the reaction, the pH of the mixture is then adjusted to 7–8 with diluted hydrochloric acid. The desired product, S-methyl-N-hydroxythioacetimidate, is recovered by filtration at −5° C. An additional amount of product can be recovered from the filtrate by extraction with methylene chloride. The crude product is analyzed by liquid chromatography to determine product purity. A crude product yield and pure product yield can then be calculated. In addition to the above process in which either acetaldoxime or biacetyl monoxime is used as the starting oxime reactant, compounds such as 3-hydroxyimino-2,4-pentanedione can be chlorinated by this process to form dichloroformaldoxime, which can further react with a mercaptide salt to form a cyclic oximino compound useful as an intermediate to carbamate insecticides. It is to be understood that variations in reactants, process conditions and manipulative steps can be used as known in the art.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactants and reagents may be initially introduced into the reaction zone batchwise or it may be continuously or intermittently introduced in such zone during the course of the process. Means to introduce and/or adjust the quantity of reactants introduced, either intermittently or continuously, into the reaction zone during the course of the reaction can be conveniently utilized in the process, especially to maintain the desired molar ratio of the aqueous medium, reactants and reagents.

The 1-organothioaldoxime compounds prepared according to the process of this invention are useful as intermediates in the preparation of pesticides. The 1-organothioaldoxime compounds may also be useful in other applications well known to those skilled in the art.

The following examples are illustrative of the present invention and are not intended as a limitation upon the scope thereof.

EXAMPLE I

Biacetyl monoxime reactant was prepared in accordance with the well-known procedure described in *Org. Synth. Coll.*, Vol. II, pp. 204–208. See particularly page 205 of that article wherein the biacetyl monoxime was made by bubbling ethyl nitrite into a reaction mixture consisting of methylethyl ketone and hydrochloric acid at a temperature of between 40° C. and 55° C. This procedure was followed by distilling off the alcohol formed in the reaction until a crude liquid temperature of 90° C. was reached. Purification of the crude biacetyl monoxime was then effected in accordance with the procedure described at page 205 of the journal article.

Sodium hypochlorite reactant was prepared by dissolving 50 grams (1.25 moles) of sodium hydroxide in 200 grams of water. The resulting solution was cooled to 25° C. followed by the addition of 100 grams of crushed ice. To the resulting mixture was bubbled 41.0 grams (0.58 mole) of chlorine at a temperature of 0° C. The resulting sodium hypochlorite solution (391 grams) was kept at a temperature of −5° C. until used.

50 grams (0.49 mole) of biacetyl monoxime was dissolved in 50 grams of water and the resulting mixture was cooled to a temperature of −5° C. 11.7 grams of concentrated hydrochloric acid was added to the mixture over a 5-minute period followed by the addition of 65.2 grams of the sodium hypochlorite solution over a 60 minute period with continuous stirring. An additional 11.7 grams of concentrated hydrochloric acid was then added in a similar manner followed by the addition of another 65.2 grams of the sodium hypochlorite solution in a similar manner with continuous stirring. The alternate feedings of concentrated hydrochloric acid and the sodium hypochlorite solution were maintained for a period of six hours until a total of 70 grams of concentrated hydrochloric acid and 391 grams of the sodium hypochlorite solution had been added. The reaction mixture was then stirred for an additional 15 minutes after the additions were completed at a temperature of −5° C. to −10° C. A sodium methyl mercaptide solution was prepared by dissolving 30 grams (0.62 mole) of methyl mercaptan in a caustic solution containing 44 grams of sodium hydroxide in 50 grams of water. The mercaptide solution was fed directly into the reaction mixture with continuous stirring over a 15 minute period at a temperature of −5° C. The resulting reaction mixture was stirred for an additional 45 minutes at the same temperature and then neutralized to pH 7.5 with diluted hydrochloric acid. The crystalline methyl hydroxythioacetimidate product was recovered at a temperature of −5° C. by filtration and drying to give 39.6 grams of product having a melting point of 90° C. to 93° C. The methyl hydroxythioacetimidate product purity was analyzed as being 95.5% by liquid chromatography.

The filtrate was further extracted with methylene chloride to give an additional 4.8 grams of crystalline methyl hydroxythioacetimidate product. The product purity was analyzed as being 79.5% by liquid chromatography.

The overall crude product yield was 85.43% based on the weight of biacetyl monoxime reactant. The overall pure product yield was 80.12% based on the weight of biacetyl monoxime reactant.

COMPARISON EXAMPLE A

Biacetyl monoxime reactant was prepared in the same manner as described in Example I.

391 grams of sodium hypochlorite solution was prepared in the same manner as described in Example I.

50 grams (0.49 mole) of biacetyl monoxime was dissolved in 50 grams of water and the resulting mixture was cooled to a temperature of −5° C. Over a period of 60 minutes, 130.3 grams of the sodium hypochlorite solution was added to the mixture with continuous stirring. An additional 130.3 grams of the sodium hypochlorite solution was then added in a similar manner with continuous stirring. The feeding of the sodium hypochlorite solution was maintained for a period of three hours until a total of 391 grams of the sodium hypochlorite solution had been added. The reaction mixture was then stirred for an additional 15 minutes after the additions were completed at a temperature of −5° C. to −10° C. A sodium methyl mercaptide solution was prepared by dissolving 30 grams (0.62 mole) of methyl mercaptan in a caustic solution containing 44 grams of sodium hydroxide in 50 grams of water. The mercaptide solution was fed directly into the reaction mixture with continuous stirring over a 15 minute period at a temperature of −5° C. The resulting reaction mixture was stirred for an additional 45 minutes at the same temperature and then neutralized to pH 7.5 with diluted hydrochloric acid. The crystalline methyl hydroxythioacetimidate product was recovered at a temperature of −5° C. by filtration and drying to give 23.0 grams of product having a melting point of 85° C. to 88° C. The methyl hydroxythioacetimidate product purity was analyzed as being 95.0% by liquid chromatography.

The filtrate was further extracted with methylene chloride to give an additional 9.2 grams of crystalline methyl hydroxythioacetimidate product. The product purity was analyzed as being 61.3% by liquid chromatography.

The overall crude product yield was 61.96% based on the weight of biacetyl monoxime reactant. The overall pure product yield was 52.89% based on the weight of biacetyl monoxime reactant.

EXAMPLE II 391 grams of sodium hypochlorite solution was prepared in the same manner as described in Example I.

28.5 grams (0.48 mole) of commercially available acetaldoxime was dissolved in 50 grams of water and the resulting mixture was cooled to a temperature −5° C. Into the mixture was added 50 grams of concentrated hydrochloric acid followed by the addition of 361 grams of the sodium hypochlorite solution over a 60 minute period with continuous stirring. The reaction mixture was then stirred for an additional 10 minutes after the additions were completed at a temperature of −5° C. to −10° C. A sodium methyl mercaptide solution was prepared by dissolving 26 grams (0.54 mole) of methyl mercaptan in a caustic solution containing 28 grams of sodium hydroxide in 56 grams of water. The mercaptide solution was fed directly into the reaction mixture with continuous stirring over a 15 minute period at a temperature of 0° C. The resulting reaction mixture was stirred for an additional 15 minutes at the same temperature and then neutralized to pH 7.5 with diluted hydrochloric acid. The crystalline methyl hydroxythioacetimidate product was recovered at a temperature of 0° C. by filtration and drying and then redissolved in acetone, filtered and dried again to give 35.0 grams of product having a melting point of 92° C. to 94° C. The methyl hydroxythioacetimidate product purity was analyzed as being 98.0% by liquid chromatography.

The filtrate was further extracted with methylene chloride to give an additional 7.2 grams of crystalline methyl hydroxythioacetimidate product. The product purity was analyzed as being 80.0% by liquid chromatography.

The overall crude product yield was 83.19% based on the weight of acetaldoxime reactant. The overall pure product yield was 78.97% based on the weight of acetaldoxime reactant.

COMPARISON EXAMPLE B 29.0 grams (0.49 mole) of commercially available acetaldoxime was added dropwise over a 20 minute period to 710 grams of commercially available sodium hypochlorite solution containing 0.5 mole of sodium hypochlorite with continuous stirring at a temperature of −5° C. The resulting reaction mixture was then stirred for an additional 15 minutes after the additions were completed at a temperature of 0° C. A sodium methyl mercaptide solution was prepared by dissolving 26 grams (0.54 mole) of methyl mercaptan in a caustic solution containing 27 grams of sodium hydroxide in 54 grams of water. The mercaptide solution was fed directly into the reaction mixture with continuous stirring over a 15 minute period at a temperature of 0° C. The resulting reaction mixture was stirred for an additional 10 minutes at the same temperature and then neutralized to pH 7.0 with diluted hydrochloric acid. The crystalline methyl hydroxythioacetimidate product was recovered at a temperature of 0° C. by filtration and drying and then redissolved in acetone, filtered and dried again to give 12.0 grams of product having a melting point of 93° C. to 94° C. The methyl hydroxythioacetimidate product purity was analyzed as being 96.0% by liquid chromatography.

The filtrate was further extracted with methylene chloride to give an additional 3.5 grams of crystalline methyl hydroxythioacetimidate product. The product purity was analyzed as being 80.0% by liquid chromatography.

The overall crude product yield was 30.03% based on the weight of acetaldoxime reactant. The overall pure product yield was 27.75% based on the weight of acetaldoxime reactant.

EXAMPLE III

Biacetyl monoxime reactant was prepared in the same manner as described in Example I.

40 grams (0.40 mole) of biacetyl monoxime was dissolved in 50 grams of water and the resulting mixture was cooled to a temperature of 0° C. 17.5 grams of concentrated hydrochloric acid was added to the mixture over a 5 minute period followed by the addition of 110.75 grams of commercially available calcium hypochlorite solution containing 0.3 mole of calcium hypochlorite over a 60 minute period with continuous stirring. An additional 17.5 grams of concentrated hydrochloric acid was then added in a similar manner followed by the addition of another 110.75 grams of the calcium hypochlorite solution in a similar manner with continuous stirring. The alternate feedings of concentrated hydrochloric acid and the calcium hypochlorite solution were maintained for a period of four hours until a total of 70 grams of concentrated hydrochloric acid and 443 grams of the calcium hypochlorite solution had been added. The reaction mixture was then stirred for an additional 15 minutes after the additions were completed at a temperature of −5° C. A sodium methyl mercaptide solution was prepared by dissolving 30 grams (0.62 mole) of methyl mercaptan in a caustic solution containing 44 grams of sodium hydroxide in 50 grams of water. The mercaptide solution was fed directly into the reaction mixture with continuous stirring over a 15 minute period at a temperature of −5° C. The resulting reaction mixture was stirred for an additional 45 minutes at the same temperature and then neutralized to pH 7.5 with diluted hydrochloric acid. The crystalline methyl hydroxythioacetimidate product was recovered at a temperature of −5° C. by filtration and drying to give 26.7 grams of product having a melting point of 91° C. to 93° C. The methyl hydroxythioacetimidate product purity was analyzed as being 90.6% by liquid chromatography.

The filtrate was further extracted with methylene chloride to give an additional 5.9 grams of crystalline methyl hydroxythioacetimidate product. The product purity was analyzed as being 79.2% by liquid chromatography.

The overall crude product yield was 78.41% based on the weight of biacetyl monoxime reactant. The overall pure product yield was 69.42% based on the weight of biacetyl monoxime reactant.

What is claimed is:

1. A process for preparing an organothioaldoxime compound of the formula:

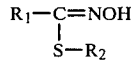

by the steps of:
(a) reacting an aldoxime of the formula:

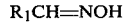

or an α-hydroxyiminoketone of the formula:

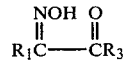

with an alkaline hypohalite in an acidic medium to form the corresponding 1-haloaldoxime, said acidic medium comprising an acid added in an amount of from about 0.5 to about 4.0 equivalents for each mole of alkaline hypohalite used; and
(b) reacting said 1-haloaldoxime with an alkali metal mercaptide salt of the formula:

to form said organothioaldoxime compound, wherein the reactions of said steps (a) and (b) are conducted in an aqueous medium and wherein M denotes an alkali metal cation and $R_1$, $R_2$ and $R_3$ are individually alkyl, alkoxyalkyl, cycloalkyl, phenyl or phenylalkyl, all of which may be either unsubstituted or substituted with one or more alkyl, halo, alkoxy, cyano, nitro or dialkylamino substituents.

2. The process of claim 1 wherein the reactions of steps (a) and (b) are carried out at a temperature or between about −20° C. and about 40° C.

3. The process of claim 1 wherein said acidic medium comprises an acid selected from the group consisting of hydrochloric acid, sulfuric acid, phosphoric acid, benzenesulfonic acid, toluenesulfonic acid, acetic acid and propionic acid.

4. The process of claim 1 wherein the acidic medium comprises an acid added in an amount of from about 1 to about 2 equivalents for each mole of alkaline hypohalite used.

5. The process of claim 1 wherein the alkaline hypohalite is selected from the group consisting of sodium hypochlorite, calcium hypochlorite and potassium hypochlorite.

6. The process of claim 1 wherein the alkaline hypohalite is employed in an amount of from about 10 to about 25 percent molar excess based on the total weight of aldoxime or α-hydroxyiminoketone reactant.

7. The process of claim 1 wherein the alkaline hypohalite is employed in an amount of from about 15 to about 20 percent molar excess based on the total weight of aldoxime or α-hydroxyiminoketone reactant.

8. The process of claim 1 wherein the aqueous medium is water.

9. The process of claim 1 wherein the aldoxime is acetaldoxime.

10. The process of claim 1 wherein the α-hydroxyiminoketone is biacetyl monoxime.

11. The process of claim 1 wherein the aldoxime or α-hydroxyiminoketone is employed in an amount of from about 5 to about 75 weight percent based on the total weight of the aqueous medium.

12. The process of claim 1 wherein the aldoxime or α-hydroxyiminoketone is employed in an amount of from about 10 to about 25 weight percent based on the total weight of the aqueous medium.

13. The process of claim 1 wherein the 1-haloaldoxime is acetylhydroxamoyl chloride.

14. The process of claim 1 wherein the alkali metal mercaptide salt is sodium methyl mercaptide.

15. The process of claim 1 wherein the alkali metal mercaptide salt is employed in an amount of from about stoichiometric to about 50 percent molar excess based on the total weight of 1-haloaldoxime.

16. The process of claim 1 wherein the alkali metal mercaptide salt is employed in an amount of from about 5 to about 25 percent molar excess based on the total weight of 1-haloaldoxime.

17. The process of claim 1 wherein the organothioaldoxime is S-methyl-N-hydroxythioacetimidate.

18. The process of claim 1 wherein $R_1$, $R_2$ and $R_3$ are individually cyanoalkyl or nitroalkyl having from one to eight carbon atoms.

19. The process of claim 1 wherein $R_1$, $R_2$ and $R_3$ are individually methyl, ethyl or propyl.

20. The process of claim 1 wherein $R_1$, $R_2$ and $R_3$ are methyl.

21. The process of claim 1 wherein the reactions of steps (a) and (b) are carried out at a temperature of between about −10° C. and about 15° C.

22. The process of claim 1 wherein the reaction time of step (a) is 6 hours.

* * * * *